US012642467B2

(12) United States Patent
Donin et al.

(10) Patent No.: US 12,642,467 B2
(45) Date of Patent: Jun. 2, 2026

(54) SYSTEM AND METHOD OF PREDICTING A NEUROPSYCHOLOGICAL STATE OF A USER

(71) Applicant: THE FOURTH DIMENSION GAMING LTD, Petah Tikva (IL)

(72) Inventors: Dov Donin, Petah Tikva (IL); Amit Cohen, Holon (IL); Nirit Krakover, Shaarei Tikva (IL); Yuval Oded, Tel Aviv (IL)

(73) Assignee: THE FOURTH DIMENSION GAMING LTD, Petah Tikva (IL)

( * ) Notice: Subject to any disclaimer, the term of this patent is extended or adjusted under 35 U.S.C. 154(b) by 417 days.

(21) Appl. No.: 18/462,845

(22) Filed: Sep. 7, 2023

(65) Prior Publication Data

US 2024/0074683 A1 Mar. 7, 2024

Related U.S. Application Data

(60) Provisional application No. 63/404,204, filed on Sep. 7, 2022.

(51) Int. Cl.
| | |
|---|---|
| *A61B 5/16* | (2006.01) |
| *A61B 5/00* | (2006.01) |
| *A61B 5/1171* | (2016.01) |
| *G06N 20/00* | (2019.01) |

(52) U.S. Cl.
CPC ............ *A61B 5/165* (2013.01); *A61B 5/0077* (2013.01); *A61B 5/1176* (2013.01); *A61B 5/163* (2017.08); *A61B 5/443* (2013.01); *A61B*

*5/486* (2013.01); *A61B 5/7203* (2013.01); *A61B 5/7275* (2013.01); *G06N 20/00* (2019.01)

(58) Field of Classification Search
CPC ........... A61B 5/16; A61B 5/165; A61B 5/742; A61B 5/72; A61B 5/7275
See application file for complete search history.

(56) References Cited

U.S. PATENT DOCUMENTS

| | | | | |
|---|---|---|---|---|
| 11,717,686 | B2 * | 8/2023 | Poltroak | ................ A61B 5/381 600/14 |
| 12,102,431 | B2 * | 10/2024 | Ambeck-Madsen | ........................ A61B 5/14546 |
| 12,186,081 | B2 * | 1/2025 | Junquera | .................. G09B 5/06 |
| 2013/0096408 | A1 * | 4/2013 | He | ........................ A61B 5/4094 600/378 |
| 2013/0216989 | A1 * | 8/2013 | Cuthbert | ............... A61B 5/1113 434/238 |
| 2016/0012530 | A1 * | 1/2016 | Gardner | ................. G06Q 40/04 705/37 |

(Continued)

*Primary Examiner* — Kurt Fernstrom

(74) *Attorney, Agent, or Firm* — PEARL COHEN ZEDEK LATZER BARATZ LLP

(57) ABSTRACT

Systems and methods of predicting a neuropsychological state of a user, including: monitoring the user, by at least one camera coupled to a processor, wherein the processor is to determine user characteristics based on input from the at least one camera, correcting, by the processor, at least one of the determined user characteristics, wherein the correction is applied to at least one of movement data and lighting data, applying a machine learning (ML) algorithm to predict a neuropsychological state of the user, wherein the ML algorithm is trained on cognitive reactions and of the user, and adjusting output of the user's media based on the predicted neuropsychological state of the user.

20 Claims, 3 Drawing Sheets

(56) References Cited

U.S. PATENT DOCUMENTS

| | | | |
|---|---|---|---|
| 2018/0075772 A1* | 3/2018 | Carr ...................... | G09B 19/00 |
| 2019/0189025 A1* | 6/2019 | Angelopoulos ........ | G16H 20/10 |
| 2019/0239791 A1* | 8/2019 | Beck ...................... | A61B 5/163 |
| 2020/0008725 A1* | 1/2020 | Bach ........................ | A61B 5/16 |
| 2020/0294670 A1* | 9/2020 | Kotikela ................ | G16H 50/30 |
| 2021/0194985 A1* | 6/2021 | Gilbert .................. | A61B 5/024 |
| 2021/0338140 A1* | 11/2021 | Amir ...................... | A61B 5/398 |
| 2022/0133194 A1* | 5/2022 | Bach ................... | A61B 5/6801 |
| | | | 600/544 |
| 2022/0183620 A1* | 6/2022 | Mavroeidis ............. | A61B 5/01 |
| 2023/0104450 A1* | 4/2023 | Garriga Calleja ..... | G16H 50/20 |
| | | | 705/2 |
| 2023/0148923 A1* | 5/2023 | Abrams .............. | A61B 5/4064 |
| | | | 600/408 |

* cited by examiner

100

CONTROLLER

OPERATING SYSTEM

105

115

MEMORY

125

EXECUTABLE CODE

120

STORAGE SYSTEM

INPUT DEVICES

OUTPUT DEVICES

135

140

130

COMMUNICATION UNIT

145 monitoring the user, by at least one camera coupled to a processor, wherein the processor is to determine user characteristics based on input from the at least one camera

301 correcting, by the processor, at least one of the determined user characteristics, wherein the correction is applied to at least one of movement data and lighting data

302 applying a ML algorithm to predict a neuropsychological state of the user 303                                                    304 adjusting output of the user's media based on the predicted neuropsychological state of the user

Fig. 3

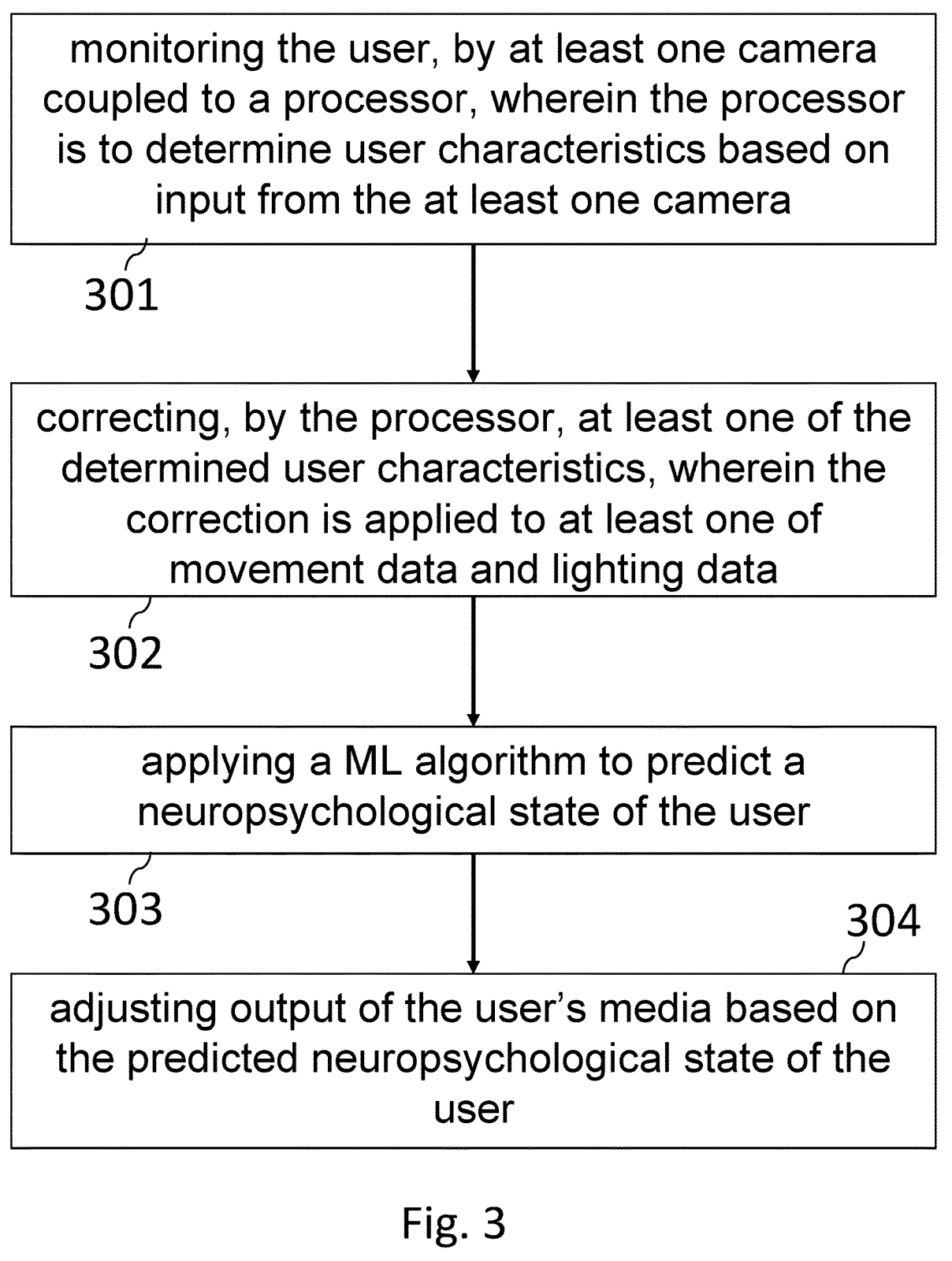

SYSTEM AND METHOD OF PREDICTING A NEUROPSYCHOLOGICAL STATE OF A USER

FIELD OF THE INVENTION

The present invention relates to human-machine interfaces. More specifically, the present invention relates to systems and methods of predicting a neuropsychological state of a user based on biofeedback input for a human-machine interface.

BACKGROUND

There is a need for a scalable utilization of biofeedback and/or psychophysiological data collection/analysis within electronic games on various platforms such as personal computers, laptops, smartphones, video-game consoles, virtual reality devices, and the like.

Previous biofeedback measurement usually relied on instruments attached to humans (such as electroencephalogram (EEG), Pulse Oximeter, Blood Oxygen Saturation Monitor, and the like) or a limited measurement achieved with a multi-camera system (such as Kinect™). For that reason, usage of human biofeedback measurement in electronic gaming is rare as there are no instruments attached to user.

Current commercial use in the gaming industry are typically incompatible with available biofeedback household measurement devices, including but not limited to smartwatches, due to, for example, devices inaccuracy in reading physiologically credible and consequential data, significant reading delay and relatively long reading intervals.

Smartwatches and other biofeedback measuring devices may not be easy to commercially spread due to, for example, their high cost and/or requirement for embedded hardware that can be required for their use in addition to the main gaming platform.

Usage of biofeedback analysis using video cameras for electronic games consoles such as Kinect™ can be limited to multiple cameras setup, typically require being mounted on a stable and fixed device and can have difficulties with changes of the player's face angle with respect to the cameras. Currently available camera biofeedback devices may not be optimized for changes in light, surrounding, screen reflections, light frequency and/or interruptions.

Current electronic games using biofeedback measurement devices may support only a single biofeedback measurement device.

Another difficulty can be a lack of technology to accumulate information from different biofeedback measurement devices for the purpose of enhancing user experience for electronic games, simulators and other types of media.

SUMMARY OF THE INVENTION

There is thus provided, in accordance with some embodiments of the invention, a method of predicting a neuropsychological state of a user, including: monitoring the user, by at least one camera coupled to a processor, wherein the processor is to determine user characteristics based on input from the at least one camera, correcting, by the processor, at least one of the determined user characteristics, wherein the correction is applied to at least one of movement data and lighting data, applying a machine learning (ML) algorithm to predict a neuropsychological state of the user, wherein the ML algorithm is trained on cognitive reactions and/or decision-making process of the user, and adjusting output of the user's media based on the predicted neuropsychological state of the user.

In some embodiments, the ML algorithm combines the corrected user characteristics for a particular user. In some embodiments, the predicted neuropsychological state of the user is personalized for the user and creates a baseline as a reference for enhancing future predictions. In some embodiments, the user characteristics are determined based on at least one of: photoplethysmography (PPG), facial recognition, RGB detection, and voice recognition.

In some embodiments, the user characteristics are determined based on at least one of: eye movement recognition, pupil movement recognition, skin pigmentation micro-change detection, and body language recognition. In some embodiments, correction of the lighting data is carried out by at least one of: angle adjustment and light frequency noise cancelation algorithms.

In some embodiments, correction of at least one of the determined user characteristics is applied to skin pigmentation micro-change detection. In some embodiments, biofeedback is received from at least one additional sensor. In some embodiments, at least one user characteristics is compared to characteristics of another user.

There is thus provided, in accordance with some embodiments of the invention, a system for prediction of a neuropsychological state of a user, including: a processor, and at least one camera coupled to the processor, wherein the at least one camera is configured to monitor the user, and wherein the processor is configured to: determine user characteristics based on input from the at least one camera, correct at least one of the determined user characteristics, wherein the correction is applied to at least one of movement data and lighting data, apply a machine learning (ML) algorithm to predict a neuropsychological state of the user, wherein the ML algorithm is trained on cognitive reactions and/or decision-making process of the user, and adjust output of the user's media based on the predicted neuropsychological state of the user.

In some embodiments, the ML algorithm is configured to combine the corrected user characteristics for a particular user. In some embodiments, the predicted neuropsychological state of the user is personalized for the user and creates a baseline as a reference for enhancing future predictions. In some embodiments, the user characteristics are determined based on at least one of: photoplethysmography (PPG), facial recognition, RGB detection, and voice recognition. In some embodiments, the user characteristics are determined based on at least one of: eye movement recognition, pupil movement recognition, skin pigmentation micro-change detection, and body language recognition.

In some embodiments, correction of the lighting data is carried out by at least one of: angle adjustment and light frequency noise cancelation algorithms. In some embodiments, correction of at least one of the determined user characteristics is applied to skin pigmentation micro-change detection. In some embodiments, biofeedback is received from at least one additional sensor. In some embodiments, at least one user characteristics is compared to characteristics of another user.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

FIG. 3 shows a flowchart for a method of predicting a neuropsychological state of a user, according to some embodiments of the invention.

Figure 1:
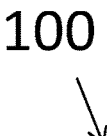
FIG. 1 shows a block diagram of an exemplary computing device, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof may occur or be performed simultaneously, at the same point in time, or concurrently.

Reference is made to FIG. 1, which is a schematic block diagram of an example computing device, according to some embodiments of the invention. Computing device 100 may include a controller or processor 105 (e.g., a central processing unit processor (CPU), a chip or any suitable computing or computational device), an operating system 115, memory 120, executable code 125, storage 130, input devices 135 (e.g. a keyboard or touchscreen), and output devices 140 (e.g., a display), a communication unit 145 (e.g., a cellular transmitter or modem, a Wi-Fi communication unit, or the like) for communicating with remote devices via a communication network, such as, for example, the Internet. Controller 105 may be configured to execute program code to perform operations described herein. The system described herein may include one or more computing device(s) 100, for example, to act as the various devices or the components shown in FIG. 2. For example, components of system 200 may be, or may include computing device 100 or components thereof.

Operating system 115 may be or may include any code segment (e.g., one similar to executable code 125 described herein) designed and/or configured to perform tasks involving coordinating, scheduling, arbitrating, supervising, controlling or otherwise managing operation of computing device 100, for example, scheduling execution of software programs or enabling software programs or other modules or units to communicate.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of similar and/or different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be a software application that performs methods as further described herein. Although, for the sake of clarity, a single item of executable code 125 is shown in FIG. 1, a system according to embodiments of the invention may include a plurality of executable code segments similar to executable code 125 that may be stored into memory 120 and cause controller 105 to carry out methods described herein.

Storage 130 may be or may include, for example, a hard disk drive, a universal serial bus (USB) device or other suitable removable and/or fixed storage unit. In some embodiments, some of the components shown in FIG. 1 may be omitted. For example, memory 120 may be a non-volatile memory having the storage capacity of storage 130. Accordingly, although shown as a separate component, storage 130 may be embedded or included in memory 120.

Input devices 135 may be or may include a keyboard, a touch screen or pad, one or more sensors or any other or additional suitable input device. Any suitable number of input devices 135 may be operatively connected to computing device 100. Output devices 140 may include one or more displays or monitors and/or any other suitable output devices. Any suitable number of output devices 140 may be operatively connected to computing device 100. Any applicable input/output (I/O) devices may be connected to computing device 100 as shown by blocks 135 and 140. For example, a wired or wireless network interface card (NIC), a universal serial bus (USB) device or external hard drive may be included in input devices 135 and/or output devices 140.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein. For example, an article may include a storage medium such as memory 120, computer-executable instructions such as executable code 125 and a controller such as controller 105. Such a non-transitory computer readable medium may be for example a memory, a disk drive, or a USB flash memory, encoding, including or storing instructions, e.g., computer-executable instructions, which when executed by a processor or controller, carry out methods disclosed herein. The storage medium may include, but is not limited to, any type of disk including, semiconductor devices such as read-only memories (ROMs) and/or random-access memories (RAMs), flash memories, electrically erasable programmable read-only memories (EEPROMs) or any type of media suitable for storing electronic instructions, including programmable storage devices. For example, in some embodiments, memory 120 is a non-transitory machine-readable medium.

A system according to embodiments of the invention may include components such as, but not limited to, a plurality of central processing units (CPUs), a plurality of graphics processing units (GPUs), or any other suitable multi-purpose or specific processors or controllers (e.g., controllers similar to controller 105), a plurality of input units, a plurality of output units, a plurality of memory units, and a plurality of storage units. A system may additionally include other suitable hardware components and/or software components. In some embodiments, a system may include or may be, for example, a personal computer, a desktop computer, a laptop computer, a workstation, a server computer, a network device, or any other suitable computing device. For example, a system as described herein may include one or more facility computing device 100 and one or more remote server computers in active communication with one or more facility computing device 100 such as computing device 100, and in active communication with one or more portable or mobile devices such as smartphones, tablets and the like.

According to some embodiments, a responsible artificial intelligence (AI) engine for electronic games is provided, based on psychophysiological data analysis derived from a webcam input.

Accordingly, a transparent, human-centered, privacy and security oriented non-biased AI (or responsible AI) engine is provided. For example, for electronic games, based on psychophysiological data analysis derived from a webcam remote photoplethysmography (PPG) implementation for game event influence insights of a player's experience. Therefore, allowing improved game development, real-time game adaptivity to player's physical or mental condition, real-time protection of player's mental health, neuro physiotherapy, cognitive and mental insight, documentation and monitoring for therapeutic use, training and assessment through gaming.

In some embodiments, systems and methods are provided for using cross-reference data, based on an artificial neural network (ANN) and/or a responsible AI engine to adjust measurements for additional physiological or psychophysiological measurement accuracy or for the purpose of human diversity bias elimination is such readings. For example, using a platform for collection of psychophysiological data from one or more input devices with a dedicated engine for the analysis processes, conclusion and/or decision making based on such data.

Figure 2:
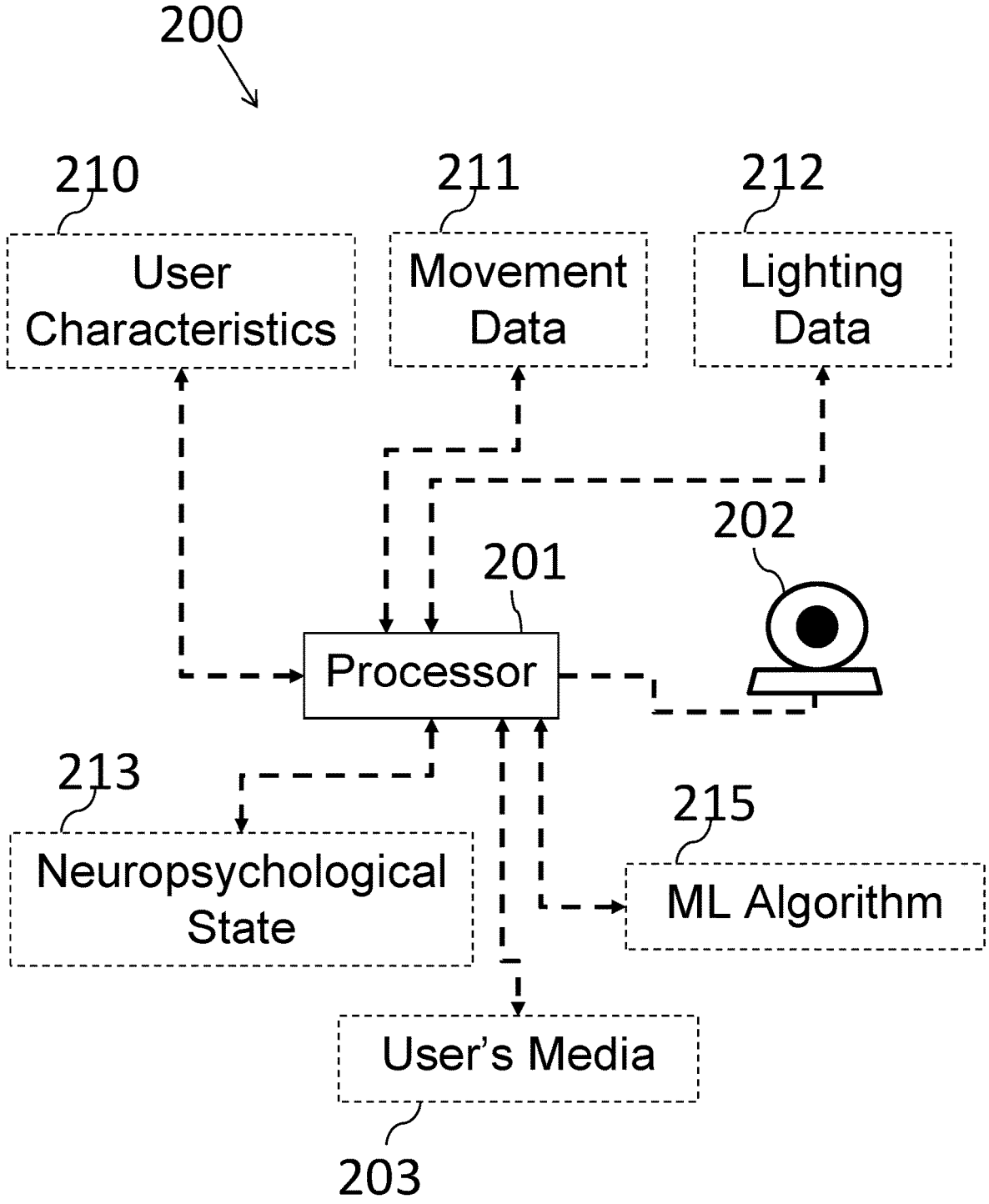
FIG. 2 shows a schematic block diagram of a system for prediction of a neuropsychological state of a user, according to some embodiments of the invention.

Reference is made to FIG. 2, which is a schematic block diagram of a system 200 for prediction of a neuropsychological state of a user, according to some embodiments of the invention. In FIG. 2, hardware elements are indicated with a solid line and the direction of arrows indicate a direction of information flow between the hardware elements.

The system 200 may include a processor 201 (e.g., such as controller 105 shown in FIG. 1) and at least one sensor 202 coupled to the processor 201. The coupling between the processor 201 and the at least one sensor 202 may be at least partially wireless (e.g., communicating over the Internet).

The system 200 may include a software development kit (SDK), for instance implemented by the processor 201, that may be integrated within electronic games. The SDK log and analyze the code, flow and events of a video game. In addition, the SDK may log the user's action within the game.

The at least one sensor 202 may be configured to monitor the user. For example, the at least one sensor 202 may monitor the user during interaction with user's media 203 (e.g., a movie or a video game).

In some embodiments, the at least one sensor 202 includes a camera, for instance a webcam or a camera that is embedded into a mobile device (e.g., a smartphone).

In some embodiments, the processor 201 is configured to determine user characteristics 210 (e.g., user's physiology parameters) based on input from the at least one sensor 202. For example, the user's physiology parameters may be read using computer vision and other instruments implemented on camera input. The user's physiology parameters may include parameters such as eye movements, body language or body movements, as well as identified changes in the user's voice (e.g., detected by a microphone). Body language reflects visible external information that originates from nervous system activity and accordingly indicates the user's state.

The received input may be from a camera (e.g., a laptop's camera or an external camera). The camera may provide a video stream to be used as a saved file for further processing or from the stream itself in real-time, where the parameters may be analyzed using ML engineering per each human parameter, or user characteristics. For example, the ML algorithm is trained on cognitive reactions and/or decision-making process of the user (e.g., while playing a game).

The ML algorithm may be trained based on a set of recorded cognitive reactions of a variety of users which may include asking a variety of questions and recording the micro-changes in the users' face (e.g., with a dedicated camera or other sensor). Some dedicated medical equipment may be utilized to measure physiological parameters and/or visual observation of the user.

In some embodiments, the ML algorithm may be trained with datasets of baseline values for user's neuropsychological condition. The baseline stage may be determined by a plurality of parameters, such as cognitive parameters (e.g., speed of response, understanding situations, perception, attention and/or concentration, and/or computational ability) that may be tested through various questionnaires for evaluation of a relaxed baseline stage. For example, the user is presented with tasks to count objects or specific shapes, identify an unusual image from a set of images, or identify a repeating pattern (e.g., as in the game "Simon Says").

The user's responses may be evaluated for correct answer and/or response time to determine emotional or cognitive state of the user. These evaluated parameters may be weighted against the level of difficulty of the question and may be accordingly compared to the average and accepted range by medical and/or psychological physicians (e.g., having an average response time of 3 second per question for shape identification).

In some embodiments, while the cognitive parameters are evaluated, a physiological baseline is monitored as well, for instance using at least one dedicated physiological sensor (e.g., to measure blood pressure, heart rate, eye movement, or speech analysis). For example, if the sensors identify a change while monitoring the user's speech such as delay in the user's conversation from fluent conversation to slower or unusual stops, or a delay between words in sentences, the corresponding physiological and/or cognitive parameters may be determined accordingly.

The result of these measurements allow to create a physiological baseline with value ranges of the user being within the accepted average (for example, a heart rate range of 60-75, and a blood pressure range of 70/80-110/120). If the user's measured parameters exceed the average ranges, an algorithmic factor may be applied to normalize and personalize the average values for a specific user in relation to all the subjects.

For example, detection of accelerated heart rate, high blood pressure or excessive sweating may result and indicate strong emotions such as a sense of threat, stress and anxiety. These are internal physiological indicators, which may appear in external visual indications, such as rapid eye movements, accelerated breathing, excessive blushing, or excessive sweating. By computing a cross-reference of various parameters, both the changes in the internal and hidden parameters as well as the visual and visible ones may be determined.

Thus, the ML algorithm may be trained on baseline values for physiological parameters, cognitive parameters and/or visual parameters (e.g., detecting change in body language).

For example, the ML algorithm may be trained when users are asked a variety of questions such as open questions, in which the subject is asked to tell a story or provide explanation/interpretation of a displayed event. Another example of questions is for closed questions in which the subject is asked to provide an answer with an absolute value (e.g., Yes/No, a number from a list, a shape from a set of shapes). Another example of questions is for questions related to the field to be examined such as questions that require a thought process (e.g., calculating the result of a mathematical equation) as an indication of cognition, or a question that triggers an emotional response (e.g., describe the happiest day of your life). Another example of questions is for formative questions, such as positive versus negative or questions formulated in a positive configuration versus questions formulated in a negative configuration.

In some embodiments, when physiological parameters and/or visual observation of the user are measured, data from different sources may be cross-referenced to find a common denominator, uniqueness, and/or anomaly and compare them for the benefit of diagnostic accuracy or to use the ability of a specific factor to identify change in a value that may not be found in another factor (e.g., measuring sweat stability or thermal signals of specific body parts). For example, data may be cross-referenced against the results obtained from medical physiological detection systems and/or from biofeedback data.

The user characteristics may be determined based on at least one of: photoplethysmography (PPG), facial recognition, RGB detection, and voice recognition. The user characteristics may also be determined based on at least one of: eye movement recognition, pupil movement recognition, skin pigmentation micro-change detection, and body language recognition.

In some embodiments, while monitoring a user, a priority is given to the most optimal data source such that lower priority sources are used as validation and/or accuracy optimizers.

In some embodiments, personal disabilities are compensated if the system recognizes characteristics issues, such as no eye movement, lack of face movement etc. Those areas may be recognized as problematic and accordingly get a lower priority or be completely ignored.

The processor 201 is configured to apply a machine learning (ML) algorithm 215, as further describe hereinafter, to analyze and adjust the determined user characteristics 210. For example, the determined user characteristics 210 may be provided as input for the ML algorithm 215.

In some embodiments, the computer vision technology in addition to an artificial neural network (ANN) and responsible AI engine allow accurate, non-bias physiological and psychophysiological remote photoplethysmography (PPG) implementation, for instance using only a simple webcam or smartphone camera. This eliminates the need for additional hardware of measurement devices, allowing every smartphone, personal computer (PC) and gaming console to become a gaming bio-responsive platform by simple means of a software update, that is easily scalable to millions of users instantly.

Thus, the system 200 may provide computer-vision based cognitive human assessment, with real-time evaluation of a user's mental health, cognitive and mental insight, documentation and monitoring for neuro-training use, training and assessment through interactions and events. Analysis based on human interaction, while using visual conference systems (VC), for example during E-Sport training and/or competition.

The AI engine may provide the process of user's telemetry with the purpose of real-time game code and/or events analysis with respect to effect on user's psychophysiological condition and learning of user's decision-making process, mental state influence factors and their effect including cognitive and motor skill capabilities during different mental states. In addition, the AI results may be used to manufacture a simulation of the user's game process and behavioral prediction and a real-time game flow responsive adaptation. Allowing to improve game design or flow using experimental tests over one or more users playing together or separately with behavioral and mental state result set.

According to some embodiments, the user characteristics 210 (e.g., user's physiology parameters) are accumulated or aggregated. The raw data from different biofeedback measurement devices may be collected by the SDK and processed locally. After processing, the metadata includes physiological information or other data from which physiological information may be extorted (i.e., video analysis intermediate results). The physiological information is extracted, accumulated and/or processed using the AI system which results in a real time physiological parameters stream.

In some embodiments, such collection and/or accumulation of biofeedback measurements allows to scale up the number of measurement devices and synchronize their outputs to a single psychophysiological analysis engine, resulting in a more comprehensive and accurate result. Thus, it may be possible to provide real-time game responsive adaptation based on user's psychophysiological state, this adaptation, unlike a controller, changes the actual flow or storyline of the game.

The processor 201 may be configured to correct at least one of the determined user characteristics 210. This correction may be applied to at least one of movement data 211 and lighting data 212 that can be determined based on data from the camera. For example, a user experiencing media from a smartphone while walking may provide shaky camera input due to movement of the device or the user as well as due to lighting changes while the user is moving. The movement data may include data on movement of a computerized device (e.g., a smartphone) such as acceleration data or angle/orientation data.

In some embodiments, biofeedback data may be collected by at least one additional sensor such as a thermic camera, a microphone for recording voice data, a heart rate sensor, as well as other non-invasive sensors.

In some embodiments, correction of at least one of the determined user characteristics 210 based on the lighting data is carried out by at least one of: angle adjustment and light frequency noise cancelation algorithms.

For example, the correction may be carried out using at least one of: trigonometric calculation corrections, distance calculations, angle calculations and their effect on shading, depth and/or sharpness correction.

In some embodiments, a combination of existing technologies is used, such as facial recognition and detection algorithms with angle adjustment video process AI, light frequency noise cancelation algorithms, motion distortion correction algorithms and/or skin pigmentation microchange detection.

For example, such combination may be applied in a calibration stage, where input for a particular user is normalized to other users from a similar group. A user having a face deformation (e.g., due to an illness) may be identified and accordingly have normalized input if the face recognition fails to identify some features.

The accumulated data of the enhanced measurements may be processed by a responsible ML algorithm 215 which perfects, cleans, improves and/or emphasizes the data in order to be used for a psychophysiological state analysis. In some embodiments, the processor is configured to apply a ML algorithm 215 to predict a neuropsychological state 213 of the user, where the ML algorithm is trained on cognitive reactions and/or decision-making process of the user. For example, the neuropsychological state 213 may include at least one of the following states: tired, stress, anxiety, confusion, hysteric, panic, fear of unknown and/or examination fear.

For example, the values for parameters of the neuropsychological state 213 (e.g., stressed state) may be provided in a scale of 1-100, where 1 is a relaxed state and 100 is a stressed state. Other values may also be in a scale of 1-100, that 1 indicates the least compatibility to that state, and 100 indicates the most compatibility to that state. In another example, other ranges for values may be used, such as 60-120 for heart rate or response time in 3-7 minutes for performance of cognitive tasks.

The ML algorithm 215 may use the received data for analysis of user factors for the video. For instance, each data source like RGB, eye movement or body language may have its own ML engineering to provide its output. To train the ML model and make it more accurate and efficient, data may be ingested alongside with the psychological analyses that provides multi-culture body language and bio-feedback definitions to the ML model. These inputs may assist in training the ML model by using supervised and/or unsupervised ML methodologies.

The stream of physiological data may be processed by the ML algorithm 215 to determine the current psychophysiological and/or mental state of the user. In some embodiments, for personalized prediction, reaction signals of a user to a particular event may be compared to reactions of other users (e.g., from a similar group of users), for instance during training.

Therefore, the system 200 may provide prediction of the human neuropsychological state 213 using low quality, unstable video camera. In some embodiments, the processing may be separated for on-premises local video analysis software development kit and cloud software services, where the system 200 allows bandwidth-optimized telemetry communication for biofeedback analysis cloud service and user endpoint.

For example, the automotive industry may utilize such predictions of the driver's neuropsychological state with an in-car camera that may capture a live feed of the driver's facial expressions. When elevated stress levels are detected, the vehicle automatically reduces its speed. Simultaneously, the driver receives an alert indicating high stress and suggestions for relaxation techniques, such as taking a break.

In another example, the gaming industry may utilize such predictions of the driver's neuropsychological state with a camera capturing the player's facial expressions in real-time while the player is engaged in the game. The video feed may accordingly be analyzed to gauge the player's stress levels, which adjusts the game's speed. If the player appears stressed, the game slows down, and conversely, the game's pace picks up if the stress levels are low. Still in the gaming industry, a camera may capture and stream pixelated images of the player's face during gameplay. This video stream may be analyzed to determine the player's stress levels, which are then used to tailor in-game advertisements. For instance, players showing signs of high stress are shown ads for food and beverages, while those appearing relaxed are targeted with lifestyle ads, such as clothing.

In some embodiments, the ML algorithm combines the corrected user characteristics for a particular user. The ML algorithm may perform cross reference of different technologies data and also of subject's detection points.

According to some embodiments, a new ML algorithm may be created for each user characteristics separately, such that a different ML algorithm may provide corresponding output for each user characteristics (e.g., eye movement or voice data). Using only a single characteristic may lead to low accuracy, so to solve this cross-reference data (CRD) may be aggregating all results from the ML algorithms into a single output. For example, the aggregated output may be level of risk by an employee or probability for Post-Traumatic Stress Disorder (PTSD) based on the context of the input.

By using cross-reference data, it may be possible to combine all user factors into the correct characteristics, since using only one user factor may not be a reliable way to analyze emotions and/or cognition. Therefore, by using various user factors may enhance or improve accuracy of the prediction.

The results of the psychophysiological and/or mental state analysis may be cross referenced with the gameplay analysis and the ML algorithm, based on both individual user's and other users' history, determine the gameplay cause to a psychophysiological effect and a psychophysiological cause to a gameplay effect.

In some embodiments, the processor 201 may be configured to adjust output of the user's media 203 based on the predicted neuropsychological state 212 of the user. For example, the user's media 203 may be a questionnaire for potential employees, where an average time to respond to each question is 3 seconds. If the processor 201 identified that the average time for a particular user to respond to each question exceeds a response time threshold (e.g., at 5 seconds) in combination with other factors such as the user being a foreigner having a different mother tongue and/or that the user is tired (e.g., based on the neuropsychological state) that user's media 203 may accordingly be adjusted such that this user gets additional time to complete the questionnaire. Thus, all potential employees may get the same starting point (e.g., as a feature of responsible AI). In this example, the ML algorithm may initially be trained to identify users with such factors and adjust the user's media 203 accordingly.

The diagnostic methodology may be based on a comparative baseline. For example, a polygraph test deals with valid/false questions, but they do not necessarily consider the different background or the mental state of the subject, fears, the effect of the examiner's appearance or tone and body language on the subject. Thus, biases are created that lead to an incorrect interpretation of the subject's answers, resulting in discrimination, exclusion. Thus, using the diagnostic methodology with comparative baseline may compensate on these factors as a "fair and non-discriminatory diagnosis methodology".

In another example, the input for a video game is adjusted for users that are determined to have a particular neuropsychological state 213 or a particular cultural group or age.

After the cause and effect of gameplay and/or psychophysiological state is established, the system 200 may provide (e.g., as a dedicated SDK) the ability to change the flow of the game in accordance with current user's mental state, previous effects, other user's effect statistics and prediction or simulation of user's behavior and/or psychophysiological responses. While a video game is described in the examples, any other form of media may be similarly applied.

In some embodiments, using the analysis of the user's state of mind, in-game message appearance, frequency, location, duration and other properties may be altered, to maximize the personalized effect on the user. For example, the system 200 may determine an initial baseline for the user, receiving additional details from the user himself, receiving details from visible sources, comparison with others diagnosed in the same category, using data from additional AI systems that identify characteristics of age, ethnicity. For example, the baseline may be obtained from the user's natural facial expressions demonstrated during small talk with the user.

In another example, the ML algorithm may be trained on behavior of various groups of users, including different cultures. If the processor determines that a particular user is having difficulty with some questions in user's media 203 of an HR questionnaire due to cultural differences associated with the language of the questionnaire (e.g., some words have different meaning in certain languages, such as in slang), the user's media 203 may accordingly be adjusted such that language of the questionnaire is changed to fit with the culture of the user. Thus, all potential employees may get the same starting point (e.g., as a feature of responsible AI).

In some embodiments, the predicted neuropsychological state of the user is personalized for the user and creates a baseline as a reference for enhancing future predictions (e.g., future predictions may be compared to this baseline). In some embodiments, the system 200 may identify the points of time or sequences of events, the hours of activity and the patterns of each person in order to provide with full knowledge regarding the performance along the day (physiological/cognitive) as a result of these effects. For example, the system may initially measure the user throughout various time periods in the day.

In some embodiments, the system 200 may create a personalized training module for each user, where the AI system learns actions and decision process of that user, during various time periods to monitor the user and create a corresponding training program that compensates emotional/temporal situations. For personalization, each user that has been analyzed by the system may be analyzed based on the user's and/or factors context, for example based on an HR credibility questioner. The analysis may be used for a specific personalized model that may be used for a specific community of people that need credibility checks.

For example, a community is a group of people that needs to have credibility check. These people may be tagged under a specific project in the system and accordingly analyzed for the total score of the community.

In some embodiments, the system 200 may be utilized in the therapeutic and/or medical world. For example, a personal baseline may be created, to enable time-based monitoring for a variety of different users or communities, such as soldiers and students. In a community of army professionals, the monitoring may be carried out from the stage of application for recruitment, a training course, assignment to duty, etc., so that at least one of the following may be achieved: initial identification of motivation and/or satisfaction, preliminary identification of fear, trauma formation and its treatment at an early stage, and accordingly prevention of the development of PTSD. In a community of students monitoring may be carried out from the kindergarten stage, grade transition, major schools, etc., so that at least one of the following may be achieved: identifying areas of interest for chosen study majors, identifying pressures or traumatic events such as violence, sexual assault, etc. and providing guidance and/or life-saving professional help.

In some embodiments, the system 200 may be utilized in the gaming world. For example, personalization of the user may be carried out to evaluate the user's situation and cognitive and/or emotional reactions during the stages of the game as well as in different games. The identification may enable a variety of applications such as: a practical research tool for game developers, which provides them with feedback on the game and the players' reactions to its various components, adding a game dimension in which the player may play against his own pressure level (in addition to the existing parameters for time, disqualifications, etc.), adding an interactive experience in which the game changes depending on the player's situation (e.g., contributes to preventing game abandonment and extending game time), and optimizing advertisements within the game as well as presenting them to the user at the times of the best "mental contact".

In some embodiments, the system 200 may be utilized in the work environment. For example, in-depth understanding of the employee/candidate may be achieved for various events or tasks, such as: preliminary identification of the risk of employee leaving as a result of dissatisfaction, reducing risk situations from the reliability and trustworthiness of an employee to various discrimination situations or hostile work reasons, incompatibility with colleagues, etc., and mental competence to improve an employee's performance and maintaining his health, through monitoring while working and dealing with tasks, challenges and the pressures exerted on the employee.

In some embodiments, the system 200 may be utilized in the cyber security world, and particularly in prevention of identity theft or deep-fakes. For example, the system may individually identify each user it samples and provide a personal profile state of their cognitive and emotional indicators. As a result of this ability, the system may identify cognitive and emotional measures that are classified as an anomaly that does not correspond to human reactions (e.g., a computer program reacts to events without emotions as humans would experience). Therefore, the system may accordingly identify impersonation and/or forgery attempts that are created using a computer and defined as fake. For example, the process of withdrawing funds or transferring funds in digital services, mainly in which visualization of the person is required (e.g., in some bank transfer procedures). The use of deepfakes, which includes generative AI, may fake a human identity both in voice and image. However, cognition and emotion detection may absolutely differentiate a fake from a real person and thus prevent malicious attacks. In some embodiments, the system may determine that the personalized state does not correspond to a human cognitive state, when the monitored data exceeds the baseline by a predefined threshold.

According to some embodiments, developers of 3rd party platforms (e.g., in the HR sector) may utilize the output of the ML algorithm for dedicated GUIs (e.g., HR GUIs). For example, an HR system may receive the output of the ML algorithm with API call sets, so as to select which calls to use according to their needs. Thus, the HR system may optimize their needs since the accuracy of finding the right candidate may improve, with additional data on candidate's neuropsychological state and/or candidate's characteristics received from the output of the ML algorithm.

Reference is made to FIG. 3, which is a flowchart for a method of predicting a neuropsychological state of a user, according to some embodiments of the invention.

In operation 301, the user is monitored, by at least one camera coupled to a processor, wherein the processor is to determine user characteristics based on input from the at least one camera.

In operation 302, at least one of the determined user characteristics is corrected, by the processor, wherein the correction is applied to at least one of movement data and lighting data.

In operation 303, a ML algorithm is applied to predict a neuropsychological state of the user, wherein the ML algorithm is trained on cognitive reactions and/or decision-making process of the user.

In operation 304, output of the user's media is adjusted based on the predicted neuropsychological state of the user.

According to some embodiments, cross-date reference may be applied for different users. For example, determining relations between background (culture, religion, gender, ethnicity, etc.), context (e.g., medical data, insurance, banking, public safety, etc.) and cognitive data (e.g., emotions data based on voice, eye movement or thermic data).

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A method of predicting a neuropsychological state of a user, the method comprising:
    monitoring the user, by at least one camera coupled to a processor, wherein the processor is to determine user characteristics based on input from the at least one camera;
    correcting, by the processor, at least one of the determined user characteristics, wherein the correction is applied to at least one of movement data and lighting data;
    applying a machine learning (ML) algorithm to predict a neuropsychological state of the user based on the determined user characteristics, wherein the ML algorithm is trained on cognitive reactions of the user; and
    adjusting output of the user's media based on the predicted neuropsychological state of the user.

2. The method of claim 1, further comprising combining, by the ML algorithm, the corrected user characteristics for a particular user.

3. The method of claim 1, wherein the predicted neuropsychological state of the user is personalized for the user and creates a baseline as a reference for enhancing future predictions.

4. The method of claim 3, further comprising determining that the personalized state does not correspond to a human cognitive state, when the monitored data exceeds the baseline by a predefined threshold.

5. The method of claim 1, wherein the user characteristics are determined based on at least one of: photoplethysmography (PPG), facial recognition, RGB detection, and voice recognition.

6. The method of claim 5, wherein the user characteristics are determined based on at least one of: eye movement recognition, pupil movement recognition, skin pigmentation micro-change detection, and body language recognition.

7. The method of claim 1, wherein correction of the lighting data is carried out by at least one of: angle adjustment and light frequency noise cancelation algorithms.

8. The method of claim 1, wherein correcting at least one of the determined user characteristics is applied to skin pigmentation micro-change detection.

9. The method of claim 1, further comprising receiving biofeedback from at least one additional sensor.

10. The method of claim 1, further comprising comparing at least one of the user characteristics to characteristics of another user.

11. The method of claim 1, wherein the ML algorithm is trained on a decision-making process of the user.

12. A system for prediction of a neuropsychological state of a user, the system comprising:
    a processor; and
    at least one camera coupled to the processor, wherein the at least one camera is configured to monitor the user; and
    wherein the processor is configured to:
    determine user characteristics based on input from the at least one camera;
    correct at least one of the determined user characteristics, wherein the correction is applied to at least one of movement data and lighting data;

apply a machine learning (ML) algorithm to predict a neuropsychological state of the user based on the determined user characteristics, wherein the ML algorithm is trained on cognitive reactions of the user; and adjust output of the user's media based on the predicted neuropsychological state of the user.

13. The system of claim 12, wherein the ML algorithm is configured to combine the corrected user characteristics for a particular user.

14. The system of claim 12, wherein the predicted neuropsychological state of the user is personalized for the user and creates a baseline as a reference for enhancing future predictions.

15. The system of claim 12, wherein the user characteristics are determined based on at least one of: photoplethysmography (PPG), facial recognition, RGB detection, and voice recognition.

16. The system of claim 15, wherein the user characteristics are determined based on at least one of: eye movement recognition, pupil movement recognition, skin pigmentation micro-change detection, and body language recognition.

17. The system of claim 12, wherein correction of the lighting data is carried out by at least one of: angle adjustment and light frequency noise cancelation algorithms.

18. The system of claim 12, wherein correction of at least one of the determined user characteristics is applied to skin pigmentation micro-change detection.

19. The system of claim 12, wherein biofeedback is received from at least one additional sensor.

20. The system of claim 12, wherein at least one of the user characteristics is compared to characteristics of another user.

\* \* \* \* \*